US00PP19022P2

(12) United States Plant Patent
Arts

(10) Patent No.: US PP19,022 P2
(45) Date of Patent: Jul. 15, 2008

(54) POINSETTIA PLANT NAMED 'ESTRELLA RED'

(50) Latin Name: *Euphoria pulcherrima*
Varietal Denomination: Estrella Red

(75) Inventor: Niels Arts, De Kwakel (NL)

(73) Assignee: Agriom B.V., De Kwakel (NL)

( * ) Notice: Subject to any disclaimer, the term of this patent is extended or adjusted under 35 U.S.C. 154(b) by 58 days.

(21) Appl. No.: 11/444,249

(22) Filed: May 31, 2006

(51) Int. Cl.
*A01H 5/00* (2006.01)

(52) U.S. Cl. ..... Plt./307
(58) Field of Classification Search ..... Plt./307
See application file for complete search history.

(56) References Cited

PUBLICATIONS

Agriom [online ]. Retreived from the Internet on May 24, 2007 at <http://www.agriom.nl/agrim.nl/agrim–eng.htm>3 pages.*

UPOV–ROM GTITM, Plant Variety Database, 2006/04, GTI Jouve Retreival Software, Citation for Euphorbia 'Estrella Red', one page.*

* cited by examiner

*Primary Examiner*—Kent L. Bell
*Assistant Examiner*—June Hwu
(74) *Attorney, Agent, or Firm*—C. A. Whealy

(57) ABSTRACT

A new and distinct cultivar of Poinsettia plant named 'Estrella Red', characterized by its uniform, strong, upright and mounded plant habit; freely branching habit; dark green-colored leaves; early flowering response; large inflorescences with dark red-colored flower bracts; and excellent post-production longevity.

1 Drawing Sheet

Botanical designation: *Euphorbia pulcherrima.*
Cultivar denomination: 'Estrella Red'.

BACKGROUND OF THE INVENTION

The present invention relates to a new and distinct cultivar of Poinsettia plant, botanically known as *Euphorbia pulcherrima* Willd., and hereinafter referred to by the name 'Estrella Red'.

The new Poinsettia is a product of a planned breeding program conducted by the Inventor in Aalsmeer, The Netherlands. The objective of the breeding program was to develop new low temperature-tolerant Poinsettia cultivars with uniform plant habit and excellent postproduction longevity.

The new Poinsettia originated from a cross-pollination made by the Inventor on Jan. 15, 2000, of a proprietary selection of Poinsettia identified as code number 99005, not patented, as the female, or seed, parent with a proprietary selection of Poinsettia identified as code number 99105-02, not patented, as the male, or pollen, parent. The cultivar Estrella Red was discovered and selected by the Inventor as a flowering plant within the progeny of the stated cross-pollination in a controlled environment in Aalsmeer, The Netherlands on Nov. 16, 2001.

Asexual reproduction of the new cultivar by terminal vegetative cuttings propagated in a controlled environment in Aalsmeer, The Netherlands since July, 2002, has shown that the unique features of this new Poinsettia are stable and reproduced true to type in successive generations of asexual reproduction.

SUMMARY OF THE INVENTION

The cultivar Estrella Red has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Estrella Red'. These characteristics in combination distinguish 'Estrella Red' as a new and distinct cultivar of Poinsettia:

1. Uniform, strong, upright and mounded plant habit.
2. Freely branching habit.
3. Dark green-colored leaves.
4. Early flowering response.
5. Large inflorescences with dark red-colored flower bracts.
6. Excellent post-production longevity.

In side-by-side comparisons conducted in Aalsmeer, The Netherlands, plants of the new Poinsettia differed from plants of the female parent primarily in flower bract size and coloration as plants of the female parent selection had larger and lighter red-colored flower bracts.

In side-by-side comparisons conducted in Aalsmeer, The Netherlands, plants of the new Poinsettia differed from plants of the male parent primarily in flower bract shape as plants of the male parent selection had lobed flower bracts. In addition, plants of the new Poinsettia had longer postproduction longevity than plants of the male parent selection.

Plants of the new Poinsettia can be compared to plants of the Poinsettia cultivar Fiscor, disclosed in U.S. Plant Pat. No. 9,364. In side-by-side comparisons conducted in Aalsmeer, The Netherlands, plants of the new Poinsettia differed from plants of the cultivar Fiscor in the following characteristics:

1. Plants of the new Poinsettia had stronger branches than plants of the cultivar Fiscor.
2. Flower bracts of plants of the new Poinsettia were mostly entire with shallow lobing whereas flower bracts of plants of the cultivar Fiscor were lobed.

3. Plants of the new Poinsettia had longer postproduction longevity than plants of the cultivar Fiscor.

BRIEF DESCRIPTION OF THE PHOTOGRAPH

The accompanying photograph illustrates the overall appearance of the new Poinsettia. The photograph shows the colors as true as it is reasonably possible to obtain in colored reproductions of this type. Colors in the photograph may differ slightly from the color values cited in the detailed botanical description which accurately describe the colors of the new Poinsettia. The photograph comprises a side perspective view of a typical flowering plant of 'Estrella Red' grown in a container.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in 13-cm containers in De Kwakel, The Netherlands during the autumn and winter in a glass-covered greenhouse and under conditions and practices which approximate those generally used in commercial Poinsettia production. During the first ten weeks of production of the plants, day and night temperatures averaged 20° C. and during the finishing production phase, day and night temperatures averaged 17° C. Light levels throughout the entire production period were about 200 Watts per square meter. Plants were pinched one time and were forced into flower under short day/long night photoperiodic conditions. Measurements and numerical values represent averages for typical flowering plants. Plants were about 17 to 18 weeks old when the photographs and the detailed description were taken.

Botanical classification: *Euphorbia pulcherrima* cultivar Estrella Red.

Parentage:

*Female, or seed, parent.*—Proprietary selection of *Euphorbia pulcherrima* identified as code number 99005, not patented.

*Male, or pollen, parent.*—Proprietary selection of *Euphorbia pulcherrima* identified as code number 99105-02, not patented.

Propagation:

*Type.*—Terminal vegetative cuttings.

*Time to initiate roots.*—About 10 to 14 days at 22° C.

*Time to produce a rooted young plant.*—About four weeks at 22° C.

*Root description.*—Fibrous, medium to thick; white in color.

*Rooting habit.*—Freely branching.

Plant description:

*Plant habit and form.*—Uniform, strong, upright and mounded plant habit; inverted triangle. Inflorescences positioned above the foliar plane. Vigorous growth habit.

*Plant height.*—About 27 cm.

*Plant diameter or spread.*—About 35 cm.

*Lateral branch description.*—Quantity: Freely branching habit, about five lateral branches develop after pinching. Length: About 18 cm. Diameter: About 6 mm. Internode length: About 1 cm to 2 cm. Strength: Strong. Texture: Smooth, glabrous. Color: 182B.

*Foliage description.*—Arrangement: Alternate, simple. Length: About 10 cm. Width: About 7 cm to 8 cm. Shape: Ovate. Apex: Acuminate to acute. Base: Obtuse. Margin: Entire or lobed. Venation pattern: Pinnate. Texture, upper and lower surfaces: Smooth, glabrous. Color: Developing foliage, upper surface: 144A. Developing foliage, lower surface: 146B. Fully expanded foliage, upper surface: 147A; venation, 59B. Fully expanded foliage, lower surface: 147B; venation, 182C. Petiole: Length: About 4 cm to 5 cm. Diameter: About 2 mm. Texture, upper and lower surfaces: Smooth, glabrous. Color, upper and lower surfaces: 59A.

*Inflorescence description.*—Inflorescence type and habit: Inflorescences are compound corymbs of cyathia with colored flower bracts subtending the cyathia. One inflorescence per lateral branch. Flowers are not fragrant. Flowers persistent. Inflorescences positioned above the foliage. Natural flowering season: Autumn/winter; inflorescence initiation and development is induced under long nyctoperiod conditions. Early flowering response, plants begin flowering about 7 weeks after the start of short day/long day photoperiodic treatments. Post-production longevity: Excellent post-production longevity; plants of the new Poinsettia maintain good substance and bract color for about six weeks under interior conditions. Inflorescence size: Diameter: About 23 cm. Height (depth): About 4 cm. Flower bracts: Quantity per inflorescence: About 15. Length, largest bracts: About 10 cm. Width, largest bracts: About 6.5 cm. Shape: Ovate. Apex: Acuminate. Base: Obtuse. Margin: Entire with shallow lobing. Texture, upper and lower surfaces: Smooth, glabrous. Venation pattern: Pinnate. Color: Developing or transitional bracts, upper surface: 53B. Developing or transitional bracts, lower surface: 53D. Fully developed bracts, upper surface: Darker than 46C. Fully developed bracts, lower surface: 46C. Venation, upper and lower surfaces: Similar to flower bract color. Bract petiole: Length: About 1 cm to 1.5 cm. Diameter: About 2 mm. Texture, upper and lower surfaces: Smooth, glabrous. Color, upper and lower surfaces: 45A. Cyathia: Quantity per corymb: About seven. Diameter of cyathia cluster: About 3 cm. Length: About 1 cm. Width: About 5 mm. Shape: Oval. Color, immature: 145A. Color, mature: 145A; towards the apex, 45C. Nectaries: Quantity per cyathium: Usually one. Size: About 6 mm. Color: 25B. Peduncles: Length: About 5 mm. Diameter: About 6 mm. Strength: Strong. Aspect: Upright. Texture: Smooth, glabrous. Color: 182D.

*Reproductive organs.*—Stamens: Quantity per cyathium: About 12. Anther shape: Oval. Anther length: About 0.5 mm. Anther color: Darker than 46A. Amount of pollen: Abundant. Pollen color: 12A. Pistils: Quantity per cyathium: About three. Pistil length: About 3 mm. Style length: About 3 mm. Style color: 46A. Stigma shape: Rounded to oval. Stigma color: 46A. Ovary color: 144A to 144B.

*Seed/fruit.*—Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 17° C. to about 35° C.

It is claimed:

1. A new and distinct Poinsettia plant named 'Estrella Red' as illustrated and described.

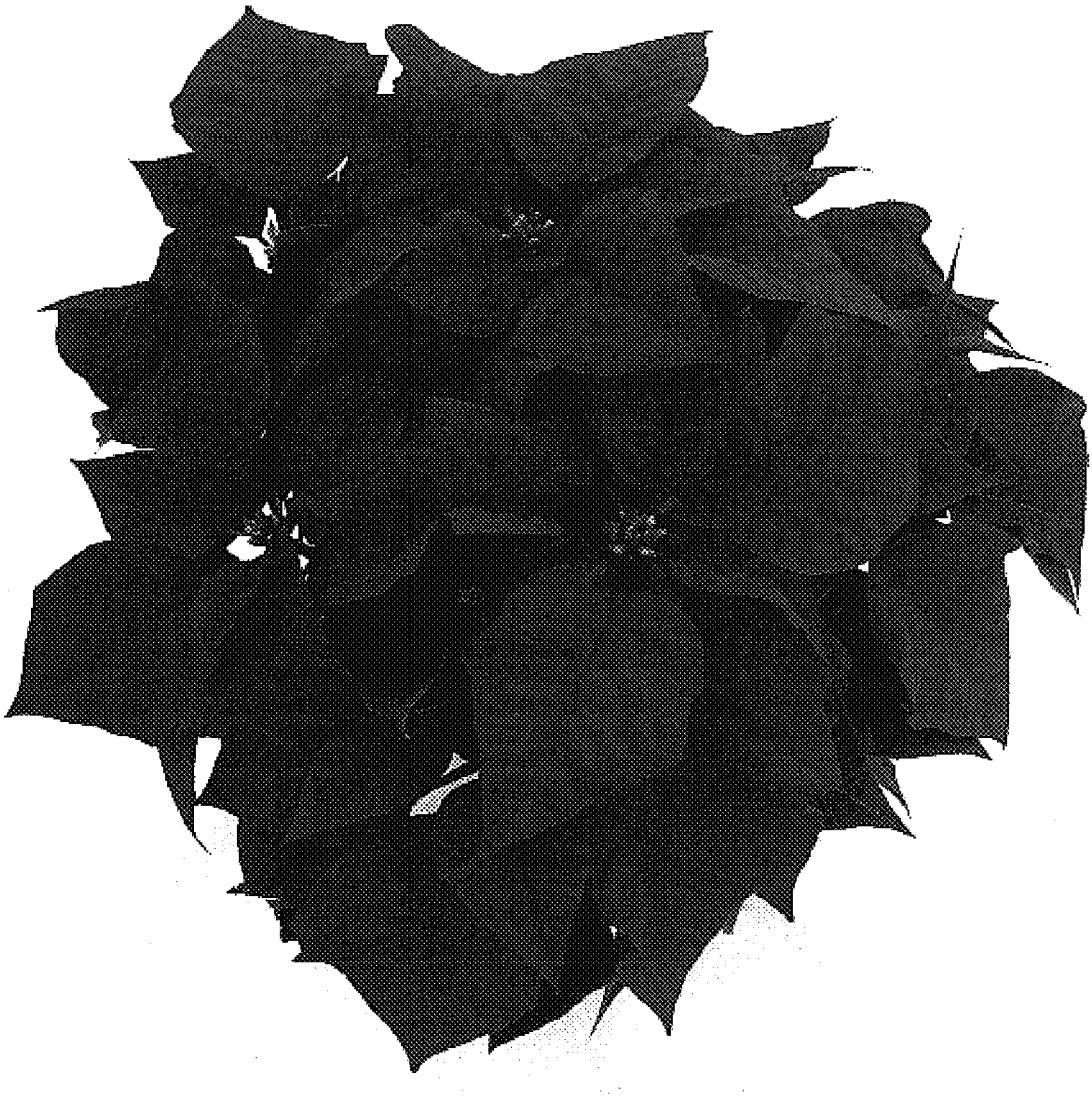

* * * * *